United States Patent [19]

Franssen et al.

[11] Patent Number: 5,150,716

[45] Date of Patent: Sep. 29, 1992

[54] SYSTEM FOR DIAGNOSIS AND STAGING OF DEMENTIA BY NEUROLOGIC EXAMINATION

[76] Inventors: Emile Franssen, 595 Main St.; Barry Reisberg, 20 Waterside Plz. #7K,. New York, N.Y. 10010

[21] Appl. No.: 646,688

[22] Filed: Jan. 28, 1991

[51] Int. Cl.$^5$ .............................................. A61B 5/103
[52] U.S. Cl. .................................................... 128/774
[58] Field of Search .............. 128/731, 733, 774, 779, 128/782

[56] References Cited

U.S. PATENT DOCUMENTS 3,322,115  5/1987  Richards .............................. 128/782

FOREIGN PATENT DOCUMENTS 1055473  11/1983  U.S.S.R. .............................. 128/774
1438695  11/1988  U.S.S.R. .............................. 128/774

OTHER PUBLICATIONS

Bowley et al. "A New Simple Detector for Achillies Reflex Measurement" Med. Biol. Eng. Jul. 1971.

Primary Examiner—Max Hindenburg
Attorney, Agent, or Firm—Gottlieb, Rackman & Reisman

[57] ABSTRACT

Deep tendon reflexes, plantar responses, muscle tone and release signs were studied as 14 individual clinical variables and as 5 summary variables in 135 aged subjects, including 27 controls, 20 subjects with mild cognitive impairment, and 88 subjects with successive stages of probable Alzheimer's disease (AD). Changes in activity of elicited responses were rated on a seven-point scale. Results were analyzed both as prevalence and mean degree of change in activity. Mild cognitive impairment was associated with a significantly higher rating than controls on a variable combining all 14 individual variables. Subjects with early AD had both higher prevalence of increased activity and increased mean scores of deep tendon reflexes and muscle tone. They had a higher prevalence of increased activity on a variable combining three release signs. Patients with late stage AD had significantly increased prevalence and mean scores of muscle tone, grasping and sucking reflexes compared with controls and early AD patients.

11 Claims, No Drawings

5,150,716

SYSTEM FOR DIAGNOSIS AND STAGING OF DEMENTIA BY NEUROLOGIC EXAMINATION

BACKGROUND OF THE INVENTION

This invention relates to methods of neurologic examination for the diagnosis and staging of the severity of dementia. The invention further relates to a method of diagnosis based upon generalized cortical, frontal and other neurologic signs.

The use of conventional neurologic examination techniques as early indicators and predictors of dementia and its progress has not been successful. Presently, dementia is diagnosed and staged by using clinical assessments of cognitive and functional capacity. For example, there are global clinical staging measures such as the Global Deterioration Scale (Reisberg, B., Ferris, S.H., de Leon, M.J. and Crook, T., 1982), the Blessed Dementia Scale and Information-Memory-Concentration Test (Blessed, G., Tomlinson, B.E. and Roth, M., 1968) and the Alzheimer's Disease Assessment Scale (ADAS) (Rosen, W., Mohs, R. and Davis, K., 1984). There are mental status assessments such as the Mini Mental State (Folstein, M.F., Folstein, S.E. and Mc Hugh, P.R., 1975), and various psychological tests such as the Auild Memory Test (Gilbert, J.G. and Levee, R.F., 1971), and the Boston Naming Test (Goodglass, H., Kaplan, E. and Weintraub, S., 1976).

All of these measurements are of limited utility in part because they depend upon the educational attainment, intelligence and skill of the subject for early diagnosis. These factors and the magnitude of cooperation can also influence staging. None of these measures are useful for staging severe dementia (Mohs, R., Kim, Y., Johns, c., Dunn, D. and Davis, K., 1986; Wilson, R.E., Kazniak, A., 1986; Reisberg, B., Ferris, S.H., de Leon, M.J. et al., 1988). Also, these measures are only a very indirect result of the actual brain changes occurring in dementia. We therefore developed the present invention of a cognition-independent system for early dementia diagnosis and staging.

Reflex phenomena such as deep tendon reflexes, paratonic muscle rigidity, and primitive reflexes (syn. release signs) have been studied in dementia, either individually or within the context of a clinical neurological examination. They have, however, not been used in a system to diagnose or stage dementia.

BRIEF DESCRIPTION OF THE PRESENT INVENTION

We have discovered that reflexes can be useful to diagnose or stage dementia. Our discovery is based upon the following method:

(1) cognition-dependent neurologic measures (such as language assessments, assessments of praxis constructional capacity, assessments of orientation laterality, etc.) are separated from cognition independent neurologic reflexes;

(2) reflex responses are carefully quantified;

(3) specific procedures, are then applied for early diagnosis and/or staging.

The invention is based upon the use of cognition-independent neurologic reflex phenomena as early diagnostic markers of dementia as well as stage specific determinants of dementia progression. The clinical syndrome of dementia is generally accompanied by more or less widespread pathologic changes in the brain. It had previously been theorized that motor activity requires participation of all parts of the central nervous system. It had also been theorized that the integrity of the motor system can sometimes better be appraised by examination of reflexes than by other measures. Alterations in reflex activity and character had been known to be among the earliest and most subtle indications of certain disturbances in neurologic function. Exaggeration of deep tendon reflexes (syn. muscle stretch reflexes) is often present with widespread cerebral disease.

Muscle tone is another reflex phenomenon and has been reported to be a common motor system abnormality related to increasing dementia severity in patients with probable AD. Paratonia (paratonic muscle rigidity or gegenhalten) is a particular form of abnormal muscle tone. It is an abnormal increase in muscle resistance to passive movement of an extremity, head or trunk. It increases with the force and the rapidity of the passive movement of the extremity, head or trunk. It occurs in dementia, but has not been utilized as a measure of increasing dementia severity. The severity of paratonia has not previously been scaled.

Primitive reflexes (syn. frontal release signs) represent another category of reflex phenomena, and are known to occur in patients with diffuse brain damage. It is generally accepted that with progression of dementia more of these signs become manifest.

Although abnormal muscle tone has been related to increased dementia severity and primitive reflexes have been known to increase with dementia severity, these measures have never been proposed to be useful for the early diagnosis or staging of dementia. Only with the application of the methodology embodied in our discovery do the measures become useful for this purpose. This methodology is summarized briefly above and described in detail below.

We have discovered that by accomplishing 1) the separation of cognitive and non-cognitive neurologic signs 2) systematically quantifying non-cognitive measures, and 3) systematically quantifying the occurrence of neurologic signs over the entire course of AD, we can use specific quantified neurologic measures in combination with a process developed by us, for the early diagnosis and staging of dementia.

One major reason for the difficulties in employing reflex phenomena as diagnostic markers in the early phase of dementia is the subtlety of the changes. We have discovered that this problem can be circumvented by careful quantification of these reflexes and by creating new measures through combining individual reflex measurements in specific groups of reflex measurements. The above-mentioned methodology can be utilized in severely impaired dementia patients who have completely lost their higher mental thought processes as well as their speech and language abilities.

It is an object of the present invention to provide a method for the modification of test procedures based on commonly used neurologic examination measures of reflexes, that results in cognition-independent test procedures effective in the early diagnosis of dementia.

It is further an object of the present invention to provide cognition independent neurologic examination tests effective in staging the progression and severity of dementia.

It is further a object of the present invention to provide a cognition independent neurologic examination method effective in tracking the progress of dementia in very severely demented patients who have reached bottom scores on cognition-dependent measures.

It is further an object of the present invention to provide a cognition independent neurologic examination method for diagnosing, tracking and staging AD based on modified existing neurologic assessment procedures. These procedures have hitherto not been used for diagnosing and staging dementia.

It is further an object of the present invention to provide a method for distinguishing between dementia subtypes, based upon the characteristic pattern of neurologic changes which we have described for the dementia of the Alzheimer's type.

DETAILED DESCRIPTION OF A PREFERRED EMBODIMENT

In accord with the present invention, measures were derived from existing neurologic examination methods (De Jong, 1979; Mayo Clinic and Mayo Foundation, 1981; Paulson, 1977) and used to assess healthy elderly individuals, elderly subjects with mild cognitive impairment and patients with dementia in all stages of clinical severity. Specific scoring methodologies were developed to rate increasing magnitudes of activity, obtained on these measures. Specifically, these measures consisted of four deep tendon reflexes (syn. muscle stretch reflexes), namely the biceps reflexes, triceps reflexes, quadriceps reflexes, and gastrocnemius-soleus reflexes; the plantar reflexes; paratonic muscle rigidity (syn. paratonia); and eight primitive reflexes, namely the tactile sucking reflex, the visual sucking reflex, the hand grasp reflex, the foot grasp reflex, the rooting reflex, the snout reflex, the glabellar blink reflex and the palmomental reflex. In accord with the present invention, six new neurologic examination measures were developed by the authors, consisting of combinations of these fourteen independent measures. A scoring methodology was developed for these six combination measures as well. In addition, instrumentation may be utilized to measure paratonic rigidity or reflex responses.

Specifically, these combination measures are: 1) a combination of all 14 individual reflexes; 2) a combination of all 4 deep tendon reflexes; 3) a combination of five primitive reflexes, namely tactile sucking reflex, visual sucking reflex, hand grasp reflex, foot grasp reflex and rooting reflex, collectively termed "prehensile release signs"; 4) a combination of three primitive reflexes, namely the snout reflex, the glabellar blink reflex and the palmomental reflex, collectively termed "nociceptive release signs"; 5) a combination of eight primitive reflexes, namely the tactile sucking reflex, visual sucking reflex, hand grasp reflex, foot grasp reflex, rooting reflex, snout reflex, glabellar blink reflex and the palmomental reflex; and 6) a combination of five primitive reflexes, collectively termed "prehensile release signs" and paratonia, namely the tactile sucking reflex, visual sucking reflex, hand grasp reflex, foot grasp reflex, rooting reflex and paratonia. In addition, a further measure was derived from individual existing neurological examination methods. One such example is a measure based upon the plantar reflex. A scoring methodology was also developed for diagnosis and staging dementia utilizing paratonic muscular rigidity.

The 7-point rating scale for neurologic examination of the present invention is as follows:

Deep tendon reflexes

1 = normal or decreased amplitude and/or speed of contraction
3 = notably increased amplitude and/or speed of contraction
5 = markedly increased amplitude and/or speed of contraction and/or with some extension of the stimulus zone
7 = greatly increase amplitude and/or speed of contraction, and/or clonos, and/or with marked extension of the stimulus zone and resulting in simultaneous contraction of adjacent joints and sometimes in mass response

Plantar response

1 = plantar flexion of the great toe
3 = no distinct flexion or extension of the great toe
5 = tonic dorsiflexion of the great toe
7 = tonic dorsiflexion of the great toe with fanning of the toes. A spinal defense reflex may occur.

Muscle tone

Paratonic rigidity (cecenhalten):
1 = paratonic rigidity not present with 10 trials (of passive, rapid, irregular, alternating flection and extension of the extremity with increasing force)
3 = occurrence of paratonic rigidity in 1 to 4 out of 10 trials
5 = paratonic rigidity in at least 5 but less than 10 times out of 10 trials
7 = paratonic rigidity is present on every attempt of passive limb manipulation.

Release signs

Sucking reflex (tactile): (15 sec. gentle stroking of the lips, with eyes closed or covered):
1 = absent
3 = slight parting of the lips
5 = lips grasp stimulus followed by distinct sucking movements
7 = very prominent sucking—lips will follow stimulus when it is withdrawn Sucking reflex (visual): (15 sec. visual stimulus):
1 = absent
3 = slight parting of the lips in response to approaching visual stimulus
5 = lips grasp approaching stimulus followed by distinct sucking movements
7 = very prominent sucking - mouth follows stimulus when it is withdrawn Hand grasp: (15 sec. stroking of palm of hand and palmar surface of fingers)
1 = absent
3 = flexion of fingers with occasional brief grasping of stimulus
5 = distinct grasping of stimulus
7 = trapping of stimulus with or without groping after stimulus; grasping may be clonic Foot grasp (tonic foot response): (15 sec. tactile stimulus)
1 = absent
3 = slight plantar flexion of the toes in response to stimulus
5 = distinct tonic plantar flexion and adduction of toes
7 = persistent prominent tonic plantar flexion and adduction of toes with arching of the foot Rooting reflex: (15 sec. of continuous tactile stimulus)

1 = absent
3 = slight movement of lips and head toward stimulus
5 = head distinctly turns toward stimulus
7 = lips and head turn prominently toward stimulus and lips try to grasp stimulus Snout reflex:
1 = absent (after at least 10 attempts)
3 = slight brief puckering of lips, occurs less than 5 times in response to 10 or more subsequent stimuli
5 = distinct puckering of lips which does not exhaust (habituate) after continuing stimuli
7 = prominent continuous pursing of lips in response to repetitive stimuli, with extension of stimulus zone - no habituation occurs Glabella blink reflex:
1 = less than 5 blinks (in response to repetitive stimuli)
3 = 5 to 10 blinks to subsequent stimuli
5 = 10 to 20 blinks to subsequent stimuli
7 = absence of habituation to repeated stimuli and extension of stimulus zone Palmomental reflex:
1 = absent (after at least 10 subsequent stimuli)
3 = 1 to 5 slight contractions of the ipsilateral mentalis muscle in response to 10 subsequent stimuli
5 = 5 to 10 distinct subsequent contractions of the ipsilateral mentalis muscle in response to 10 subsequent stimuli
7 = no habituation occurs, prominent muscle contraction, extension of stimulus zone outside the palm of the hand may occur In situations falling between the four well-defined points 1, 3, 5 and 7, intermediate numerical scores 2, 4, and 6 are used.

The inventors have discovered that the present invention can be employed to diagnose mild cognitive impairment.

When a combination measure was employed which combines the obtained score on all 14 individual measures, 80% of subjects with mild cognitive impairment as measured on the Global Deterioration Scale (GDS stage 3) had abnormal scores on this measure. Consequently, this measure is a sensitive marker for early dementia.

Of elderly subjects with mild cognitive impairment (GDS stage 3), 55% have abnormal values on the measure which combines 4 deep tendon reflexes versus 26% of cognitively normal elderly. Consequently, this combinatorial measure is useful as an early marker of dementia.

Paratonic muscle rigidity (paratonia) is not present in elderly cognitively normal subjects, but is present in 10% of individuals with mild cognitive impairment (GDS stage 3); it is present in 12% of subjects with mild dementia (GDS stage 4) of the Alzheimer type; it is present in respectively 42% of patients with moderate dementia associated with Alzheimer's disease (GDS stage 5); in 75% of patients in the severe dementia stage of Alzheimer's disease (GDS stage 6) and in 100% of patients with very severe dementia associated with Alzheimer's disease (GDS stage 7). Consequently, we have discovered that this measure is a sensitive indicator of dementia and dementia progression.

Seventy percent of elderly subjects with mild cognitive impairment (GDS stage 3) have abnormal values on a measure which combines three primitive reflexes, which we have collectively termed nociceptive reflexes, as compared to only 30% of cognitively normal subjects. Consequently, the inventors believe this measure to be useful as an early marker for dementia.

Thirty-five percent of subjects with severe dementia (GDS stage 6) have abnormal scores on a combination measure which combines 5 primitive reflexes, collectively termed "prehensile release signs." Cognitively intact subjects do not score on this measure, whereas 100% of very severely demented subjects (GDS stage 7) have abnormal scores on this measure. Consequently, this measure is an indicator of severe dementia.

Subjects who attain abnormal scores on a combination of paratonia and prehensile release signs are almost all unable to ambulate independently. Consequently, the combination of these measures is a diagnostic indicator of imminent loss of independent ambulation in dementia.

Clinical Advantages of the Assessment Procedures

This invention has accomplished the following:

(1) it provides a sensitive cognition independent method for diagnosing and staging dementia, (2) it provides the only objective, observationally based, staging instrument hitherto capable of continuously tracking the course of dementia, even into the severe stages where cognition-dependent measures bottom out, (3) it provides an instrument for evaluating motor system impairment in demented patients, (4) it improves clinical and research capacity to evaluate the benefit of psychopharmacologic intervention strategies for these patients, (5) it improves the ability of research and health professionals to track and monitor the course of deterioration of persons with severe dementia, and (6) it provides the clinician with a set of relatively rapid an simple bedside tests to evaluate severity of dementia in a patient with probable AD.

We claim:

1. The process for developing cognition independent tests for the diagnosis and staging of dementia comprising
   (a) separation of cognition-dependent measures from the clinical neurologic examination
   (b) selecting a group of cognition-independent measures from the clinical neurologic examination, more specifically, reflex phenomena, for the purpose of diagnosing and staging dementia
   (c) developing and modifying scoring methodology of cognition-independent clinical measures, specifically, reflexes
   (d) developing new neurologic measurements from specific combinations of individual quantified neurologic measurements, that is, from reflexes
   (e) utilizing these quantified individual clinical neurologic measurements as well as the combination neurologic quantified measurements to diagnose and stage dementia.

2. The method of claim 1 wherein said step of selecting a group of cognition-independent neurological tests for the sole purpose of diagnosing and staging dementia comprises the selection of specific deep tendon reflexes, plantar reflexes, partonia and primitive reflexes (release signs).

3. The method of claim 2 wherein said step of developing scoring methodology comprises the creation of scales for rating the activity of deep tendon reflexes, plantar reflexes, paratonic rigidity, and primitive reflexes.

4. A method of measuring a cognition, independent and primitive reflexes, obtaining a combination of scores from said measurements and deriving said parameter from said combination.

5. A method of measuring a cognition, independent parameter for diagnosing and staging dementia comprising the steps of measuring deep tendon reflexes selected from the group consisting of biceps reflexes, triceps reflexes, quadriceps reflexes and gastrocnemius-soleus reflexes, obtaining a combination of scores from said measurements and deriving said parameter from said combination.

6. A method of measuring a cognition, independent parameter for diagnosing and staging dementia comprising the steps of measuring prehensile primitive reflexes selected from the group consisting of tactile and visual sucking reflexes, hand grasp and foot grasp reflexes and rooting reflex, obtaining a combination of scores from said measurements and deriving said parameter from said combination.

7. A method of measuring a cognition, independent parameter for diagnosing and staging dementia comprising the steps of measuring nociceptive primitive reflexes selected from the group consisting of the snout reflex, the glabellar blink reflex and the palmomental reflex, obtaining a combination of scores from said measurements and deriving said parameter from said combination.

8. A method of measuring a cognition, independent parameter for diagnosing and staging dementia comprising the steps of measuring primitive reflexes selected from the group consisting of prehensile primitive reflexes and nociceptive reflexes, obtaining a combination of scores from said measurements and deriving said parameter from said combination of scores.

9. A method of measuring a cognition, independent parameter for diagnosing and staging dementia comprising the steps for measuring prehensile reflexes and paratonia, obtaining a combination of scores from said measurements and deriving said parameter from said combination of scores.

10. A method of measuring a cognitive, independent parameter for diagnosing and staging dementia comprising the steps of measuring the plantar reflex, obtaining a score based on said measurement and deriving said parameter from said score.

11. A method of measuring a cognitive, independent parameter for diagnosing and staging dementia comprising the steps of measuring the severity and magnitude of abnormal paratonic muscular rigidity, obtaining a score based on said measurement and deriving said parameter from said score.

* * * * *

UNITED STATES PATENT AND TRADEMARK OFFICE
CERTIFICATE OF CORRECTION

PATENT NO. : 5,150,716
DATED : September 29, 1992
INVENTOR(S) : Emile Franssen, et al It is certified that error appears in the above-indentified patent and that said Letters Patent is hereby corrected as shown below:

On the title page, item [76] Inventors: "Emile H. Franssen, 595 Main St." should read --Emile Franssen, 595 Main Street # 1102 New York, N.Y. 10044--.

Signed and Sealed this

Sixteenth Day of November, 1993

*Attest:*

BRUCE LEHMAN

*Attesting Officer*  *Commissioner of Patents and Trademarks*